US00PP34963P2

(12) United States Plant Patent
Bozanic Tanjga

(10) Patent No.: US PP34,963 P2
(45) Date of Patent: Feb. 7, 2023

(54) SHRUB ROSE PLANT NAMED 'BOZFRA221'

(50) Latin Name: *Rosa hybrida*
Varietal Denomination: 'BOZFRA221'

(71) Applicant: Biljana Bozanic Tanjga, Novi Sad (RS)

(72) Inventor: Biljana Bozanic Tanjga, Novi Sad (RS)

(73) Assignee: Pheno Geno Roses B.V.

( * ) Notice: Subject to any disclaimer, the term of this patent is extended or adjusted under 35 U.S.C. 154(b) by 0 days.

(21) Appl. No.: 17/736,634

(22) Filed: May 4, 2022

(51) Int. Cl.
*A01H 5/02* (2018.01)
*A01H 6/74* (2018.01)

(52) U.S. Cl.
USPC ..... Plt./106

(58) Field of Classification Search
USPC ..... Plt./106, 105, 107, 146, 147, 148
CPC ... A01H 5/02; A01H 5/00; A01H 6/74; A01H 6/749
See application file for complete search history.

(56) References Cited

PUBLICATIONS

Otto & Sons Nursery Rose List 2022, retrieved on Jun. 9, 2022 at https://ottoandsonsnursery.com/wp-content/uploads/2022/04/Otto.Rose_.Availability.4.9.22.pdf, pp. 1-6. (Year: 2022).*
Rosarium Lottum Dominica, retrieved on Jun. 9, 2022 at https://rosariumlottum.com/en/product/dominica-stem-rose-90-100-cm/, 5 pp. (Year: 2022).*
Spring Meadow Nursery Flowering Shrubs Starter Plants Catalog and Shrub Reference 2021-2022, retrieved on Jun. 9, 2022 at https://cdn.coverstand.com/65723/717743/fd338d123923398b32713a713f760f32e02147ea.pdf, pp. 1-2, 98. (Year: 2022).*

* cited by examiner

*Primary Examiner* — June Hwu
(74) *Attorney, Agent, or Firm* — Cassandra Bright

(57) ABSTRACT

A new and distinct cultivar of *Rosa* plant named 'BOZFRA221' is disclosed, characterized by large, orange-pink double flowers. Plants have semi-upright habits and are tolerant to rust and downy mildew. The new variety is a *Rosa*, normally produced as an outdoor garden or container plant.

2 Drawing Sheets

Figure 1:
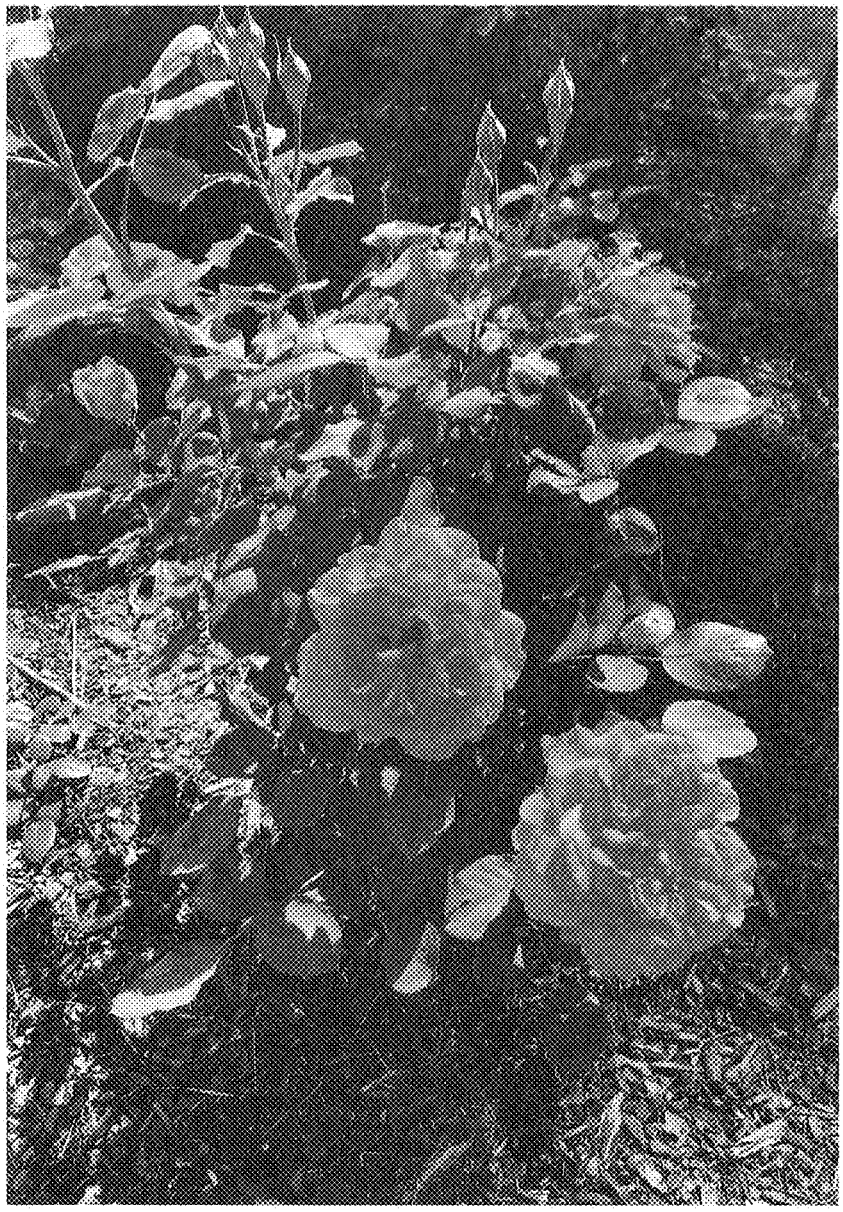

Latin name of the genus and species: *Rosa hybrida.*
Variety denomination: 'BOZFRA221'.

BACKGROUND OF THE INVENTION

The new *Rosa* cultivar is a product of a planned breeding program conducted by the inventor, Biljana Bozanic Tanjga, in Temerin, Serbia. The objective of the breeding program was to produce new profusely flowering shrub rose plants with good disease resistance, and large, vibrantly colored blooms. The cross resulting in this new variety was made during May of 2013.

The seed parent is the unpatented *Rosa* 'Clair Renaissance'. The pollen parent is the unpatented *Rosa* 'Dominica'. The new variety was discovered in June of 2014 by the inventor in a group of seedlings resulting from the 2010 crossing, in a research nursery in Temerin, Serbia.

Asexual reproduction of the new cultivar was performed by softwood cuttings at a research nursery in Mali Idjos, Serbia in 2015, and has shown that the unique features of this cultivar are stable and reproduced true to type in multiple successive generations.

SUMMARY OF THE INVENTION

The cultivar *Rosa* 'BOZFRA221' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BOZFRA221'. These characteristics in combination distinguish 'BOZFRA221' as a new and distinct *Rosa* cultivar:

1. Orange-pink flowers.
2. Large, double flowers.
3. Semi-upright habit.
4. Tolerant to rust and downy mildew.

Plants of the new cultivar 'BOZFRA221' are similar to plants of the seed parent in most horticultural characteristics, however, plants of the new cultivar 'BOZFRA221' differ in the following;

1. Plants of the new variety are not as tall as plants of the seed parent.
2. Flowers of the new variety have more petals than flowers of the seed parent.
3. Flowers of the new variety have a medium fragrance, while flowers of the seed parent have a strong, old rose fragrance.
4. Flower color of the new variety is orange-pink, while the flower color of the seed parent is light pink.

Plants of the new cultivar 'BOZFRA221' are similar to plants of the pollen parent in most horticultural characteristics, however, plants of the new cultivar 'BOZFRA221' differ in the following;

1. Plants of the new variety are about 70 cm in height, while plants of the pollen parent are about 60 to 80 cm in height.
2. Flower color of the new variety is orange-pink, while the flower color of the pollen parent is red.
3. Flowers of the new variety have more petals than flowers of the pollen parent.
4. Flowers of the new variety have a medium fragrance, while flowers of the pollen parent have a mild fragrance.
5. Plants of the new variety are re-blooming, while plants of the pollen parent bloom throughout the season.

COMMERCIAL COMPARISON

Plants of the new cultivar 'BOZFRA221' are comparable to the commercial variety *Rosa* 'Auscousin', U.S. Plant Pat. No. 25,064. The two *Rosa* varieties are similar in most horticultural characteristics; however, the new variety 'BOZFRA221' differs in the following:

1. Flowers of the new variety have a flat profile, while flowers of this comparator are mostly flat, but outermost ring of petals curve and cup interior petals.
2. The new variety has a more compact growth habit than this comparator.

BRIEF DESCRIPTION OF THE PHOTOGRAPHS

The accompanying photograph in FIG. 1 illustrates in full color a typical plant of 'BOZFRA221' grown in a 2-gallon container. Age of the plant photographed is approximately 5 months.

Figure 2:
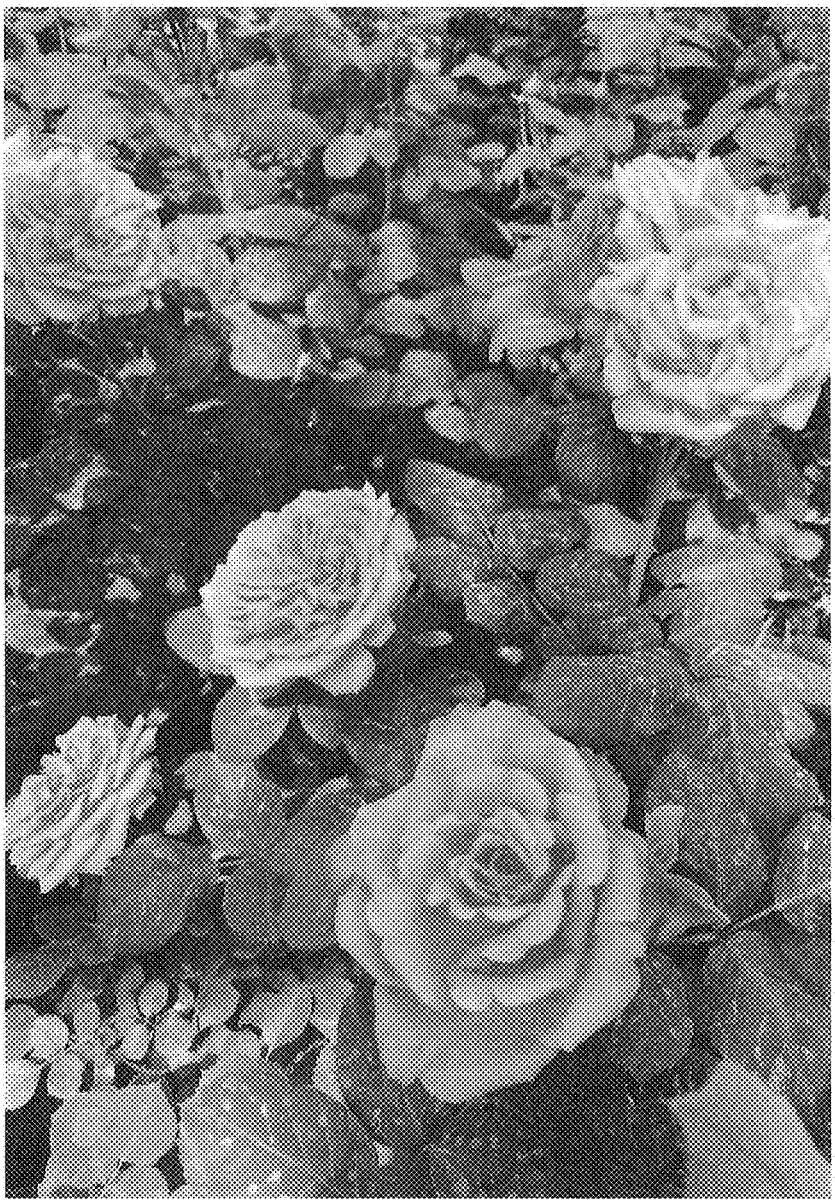

FIG. 2 illustrates a close-up view of flowers of 'BOZFRA221'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'BOZFRA221' plants grown outdoors during the Spring and Summer, in Grand Haven, Mich. The growing temperature ranged from 15° C. to 40° C. during the day and from −25° C. to 30° C. during the night. General light conditions were bright, normal sunlight. No chemical treatments were used. Measurements and numerical values represent averages of typical plant types.

Botanical classification: *Rosa hybrida* 'BOZFRA221'.

PROPAGATION

Propagation method: Softwood cuttings.
Time to initiate roots: 30 days at 20° C. in summer.
Time to produce rooted plant: 120 days at 20° C. in summer.
Root description: Good density, moderately branched, medium thickness, fibrous, and fleshy. White in color, not accurately measured using R.H.S. chart.

PLANT

Age of plant described: Approximately 2 years old.
Plant type: Perennial shrub.
Rootstock: Own roots.
Growth habit: Upwards and slightly outwards.
Plant shape: Compact, upright.
Height: 70 cm.
Plant spread: 50 cm.
Growth rate: Good.
Plant vigor: Fairly vigorous.
Branching characteristics: Basal.
Length of primary lateral branches: 55 cm.
Diameter of lateral branches: 6 mm.
Quantity of lateral branches: 10 to 12.
Internode length: 3 cm.
Stem:
- *Shape*.—Round.
- *Aspect*.—Very upright.
- *Strength*.—Strong.
- *Color*.—RHS Yellow-Green 144B.
- *Anthocyanin on young growth*.—Not present.
- *Pubescence*.—None.

Thorns:
- *Quantity*.—2 to 3 per linear cm.
- *Shape*.—Narrow, bent downward.
- *Apex*.—Acicular.
- *Base*.—Obtuse.
- *Height*.—4 mm.
- *Color, immature*.—RHS Greyed-Red 180C.
- *Color, mature*.—RHS Greyed-Red 180C.

FOLIAGE

Leaf:
- *Arrangement*.—Alternate.
- *Quantity*.—12 per lateral branch.
- *Length*.—12 cm.
- *Width*.—9 cm.

Leaflet:
- *Quantity*.—3 to 7 per leaf.
- *Terminal length*.—5 cm.
- *Terminal width*.—3.5 cm.
- *Lateral length*.—4 cm.
- *Lateral width*.—2.5 cm.
- *Shape of blade*.—Elliptic.
- *Apex*.—Acute/acuminate.
- *Base*.—Obtuse.
- *Margin*.—Serrulate. Weak undulation.
- *Texture*.—Smooth, coriaceous upper and lower surfaces.
- *Pubescence*.—None.
- *Appearance*.—Weakly glossy on upper surface. Matte lower surface.
- *Color*.—Young foliage upper side: RHS Greyed-Purple 183B, fading to Yellow-Green 152A towards center vein. Young foliage under side: RHS Greyed-Purple 183B, fading to Yellow-Green 152A towards center vein. Mature foliage upper side: RHS Yellow-Green 147A. Mature foliage under side: Near RHS Yellow-Green 147B.
- *Venation*.—Type: Pinnate. Venation color upper side: RHS Yellow-Green N144D. Venation color under side: RHS Yellow-Green N144D.

Petiole:
- *Leaf*.—Length: 3.5 cm. Diameter: 2 mm. Color, upper surface: RHS Yellow-Green N144D with tinges of Greyed-Orange 176B and Brown 200B. Color, lower surface: RHS Yellow-Green N144D. Texture: Glabrous.

*Leaflet*.—Length: 1 mm. Diameter: 1 mm. Color, upper surface: RHS Yellow-Green N144D with tinges of Greyed-Orange 176B to Brown 200B. Color, lower surface: RHS Yellow-Green N144D. Texture: Glabrous.

Stipules:
*Quantity*.—2.
*Shape*.—Linear/acicular.
*Apex*.—Acicular.
*Base*.—Fused along petiole.
*Margin*.—Entire.
*Length*.—15 mm.
*Width*.—2 mm.
*Texture*.—Smooth, both surfaces.
*Color, upper surface*.—RHS Yellow-Green 147A.
*Color, lower surface*.—RHS Yellow-Green N144D.

FLOWER

Natural flowering season: Spring through summer.
Flower type and habit: 1 to 6 blooms arranged terminally in cymes on lateral branches.
Flower form: Double flower, whorled.
*Shape*.—Round whorl.
*Diameter*.—10 cm.
*Depth*.—3 cm.
*Aspect*.—Very upright.
*Persistent or self-cleaning*.—Self-cleaning.

Bud:
*Shape*.—Ovate.
*Length*.—2.5 cm.
*Diameter*.—2 cm.
*Color*.—RHS Yellow-Green 144A with some tinges of Greyed-Red 178A.

Petals:
*Arrangement*.—Double whorl.
*Appearance*.—Vibrantly colored, recurved, with notched apices.
*Length*.—Outer whorl: 4 cm. Inner whorl: 3 cm.
*Width*.—Outer whorl: 3.5 cm. Inner whorl: 2 cm.
*Shape*.—Outer whorl: Orbicular. Inner whorl: Obovate.
*Margin*.—Entire, curled toward underside.
*Apex*.—Retuse, notched.
*Fused*.—No.
*Quantity*.—About 55.
*Texture*.—Silky and smooth.
*Color*.—When opening: Upper surface: RHS Red 51A, fading to Yellow 13B at base. Lower surface: RHS Red 54A, fading to Yellow 13B at base. Fully opened: Upper surface: RHS Red 51C, fading to Yellow 13B at base. Lower surface: RHS Red 51C, fading to Yellow 13B at base.

Petaloids:
*Shape*.—Irregular, curved.
*Arrangement*.—Whorled.
*Quantity*.—About 10.
*Margin*.—Entire to slightly crenate, curved towards underside.
*Length*.—3 cm.
*Width*.—2 cm.
*Color*.—Immature: RHS Red 51C, fading to Yellow 13B at base. Mature: RHS Red 51C, fading to Yellow 13B at base.

Sepals:
*Appearance*.—Rough, recurved toward stem.
*Arrangement*.—Whorl around base.
*Quantity*.—5.
*Shape*.—Triangular.
*Margin*.—Entire.
*Sepal extensions*.—Weak.
*Apex*.—Acuminate.
*Base*.—Fused.
*Length*.—2.5 cm.
*Width*.—1 cm.
*Texture*.—Smooth, slightly pubescent on underside.
*Color*.—Immature, upper side: RHS Yellow-Green 144A with some tinges of Greyed-Red 178A. Immature, under side: RHS Yellow-Green 144A. Mature, upper side: RHS Yellow-Green 144A with some tinges of Greyed-Red 178A. Mature, under side: RHS Yellow-Green 144A.

Calyx:
*Shape*.—Collar-like with recurved sepals arranged in a whorl.
*Length*.—2 cm.
*Diameter*.—1 cm.

Peduncle:
*Length*.—4 cm.
*Diameter*.—3 mm.
*Angle*.—Upright, 75° to 90°.
*Strength*.—Strong.
*Texture*.—Slightly prickly/stubbly.
*Color*.—RHS Yellow-Green 144A, with tinges of Greyed-Red 178A.

Fragrance: Light and sweet.

REPRODUCTIVE ORGANS

Stamens:
*Number*.—About 100.
*Filament color*.—RHS Orange-Red 34B.

Anthers:
*Length*.—2 mm.
*Shape*.—Club-like, dorsifixed.
*Color*.—RHS Yellow-Orange 16A.
*Pollen*.—Some.
*Pollen color*.—RHS Yellow-Orange 16A.

Pistil:
*Number*.—About 75.
*Length*.—12 mm.
*Style*.—Length: 11 mm. Color: RHS Yellow-Orange 16B, fading to White 155A.
*Stigma*.—Shape: Rounded. Color: RHS Yellow 8B.
*Receptacle*.—Height: 1 cm. Diameter: 1 cm. Shape: Orbicular. Texture: Smooth. Color: RHS Green 143B.

OTHER CHARACTERISTICS

Seeds and fruits: None observed.
Disease/pest resistance: Tolerant to rust (*Phragmidium mucronatum*) and downy mildew (*Peronospora sparsa*).
Temperature tolerance: Observed tolerance between −25° C. to at least 40° C. degrees.

What is claimed is:

1. A new and distinct cultivar of *Rosa* plant named 'BOZFRA221' as herein illustrated and described.

* * * * *